US00PP30946P2

(12) United States Plant Patent
Van Swieten

(10) Patent No.: US PP30,946 P2
(45) Date of Patent: Oct. 15, 2019

(54) ***PHALAENOPSIS* ORCHID PLANT NAMED 'PHALGOSEP'**

(50) Latin Name: ***Phalaenopsis* hybrid**
Varietal Denomination: PHALGOSEP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/999,891

(22) Filed: Aug. 28, 2018

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

(56) References Cited

PUBLICATIONS

UPOV hit on *Phalaenopsis* plant named, 'Phalgosep', QZ PBR 20171085, filed Apr. 24, 2017.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALGOSEP', particularly characterized by having white flowers with extra-large lips and purplish-pink shade, 1 to 2 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGOSEP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGOSEP'.

The new *Phalaenopsis* plant is a product of a planned breeding program conducted by the inventor in Bleiswijk, The Netherlands. The objective of this breeding program was to create a new *Phalaenopsis* plant with numerous attractive white flowers with extra-large white lips and purplish-pink shade, suitable for potted plant production.

The new *Phalaenopsis* plant 'PHALGOSEP' is a result of cross-pollination made by the inventor in April 2010 in Bleiswijk, The Netherlands of the proprietary female, or seed parent, *Phalaenopsis* hybrid '01-1988' (unpatented) with the proprietary male, or pollen parent, *Phalaenopsis* hybrid '01-3401' (unpatented).

The new *Phalaenopsis* was selected by the inventor as a single plant within the progeny of the stated cross-pollination in a controlled greenhouse in Bleiswijk, The Netherlands in February 2013. Asexual reproduction of the new *Phalaenopsis* plant by meristem tissue culture since 2015 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGOSEP' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALGOSEP' as a new and distinct variety of *Phalaenopsis* plant.

1) White flowers with extra-large lips and purplish-pink shade;
2) 1 to 2 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in July 2018. Colors in the photographs may differ from the color values cited in the detailed botanical description, which accurately describe the actual colors of the new variety.

DESCRIPTION OF THE NEW VARIETY

Figure 1:
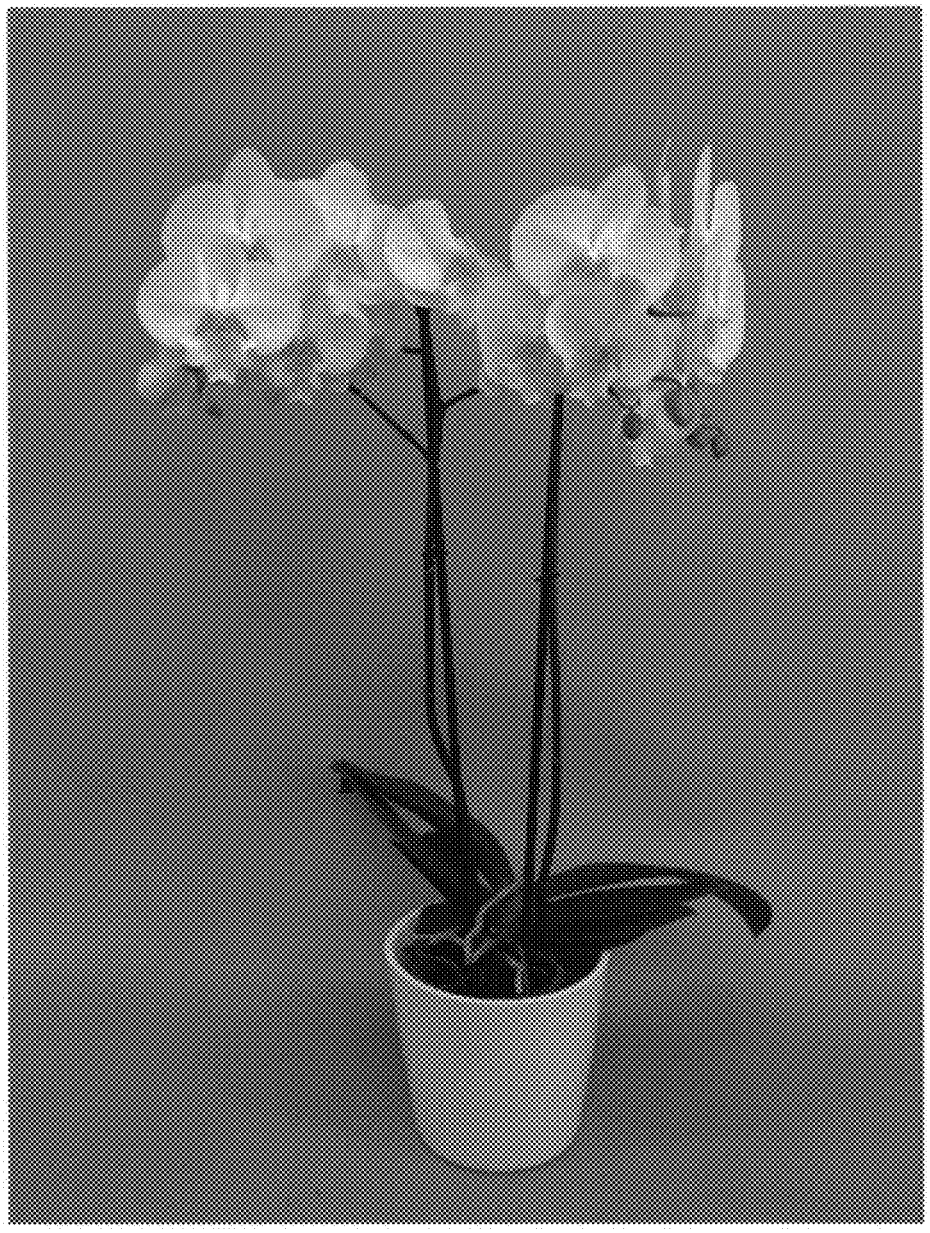
FIG. 1 shows the overall plant habit, including blooms, buds and foliage of 'PHALGOSEP'.
Figure 2:
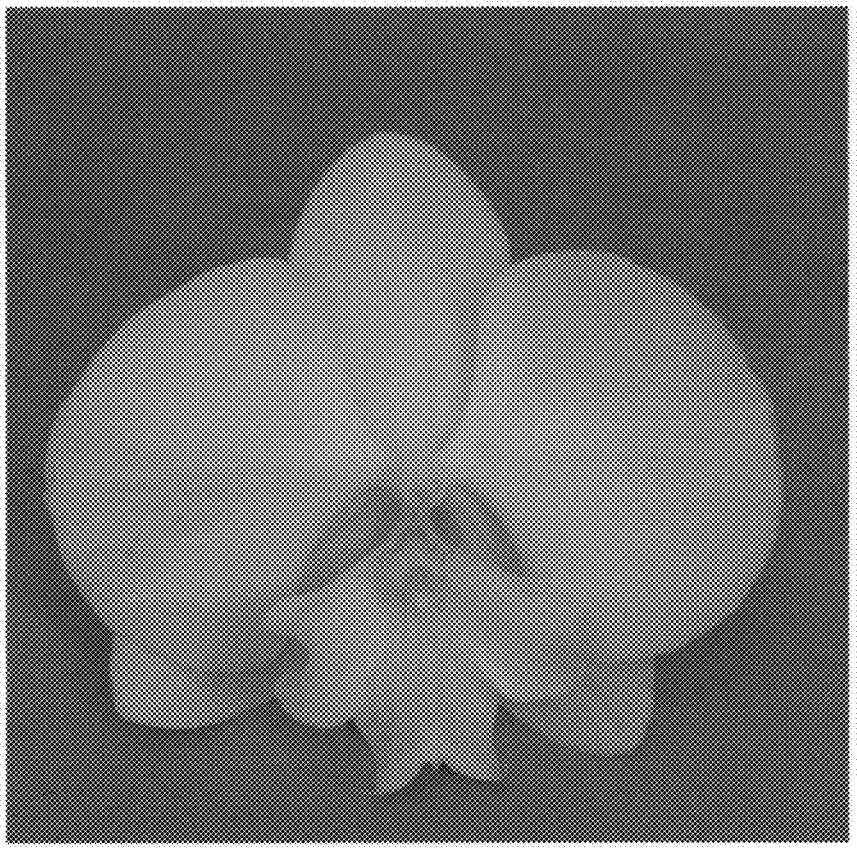
FIG. 2 shows a close-up of a flower of 'PHALGOSEP'.
Figure 3:
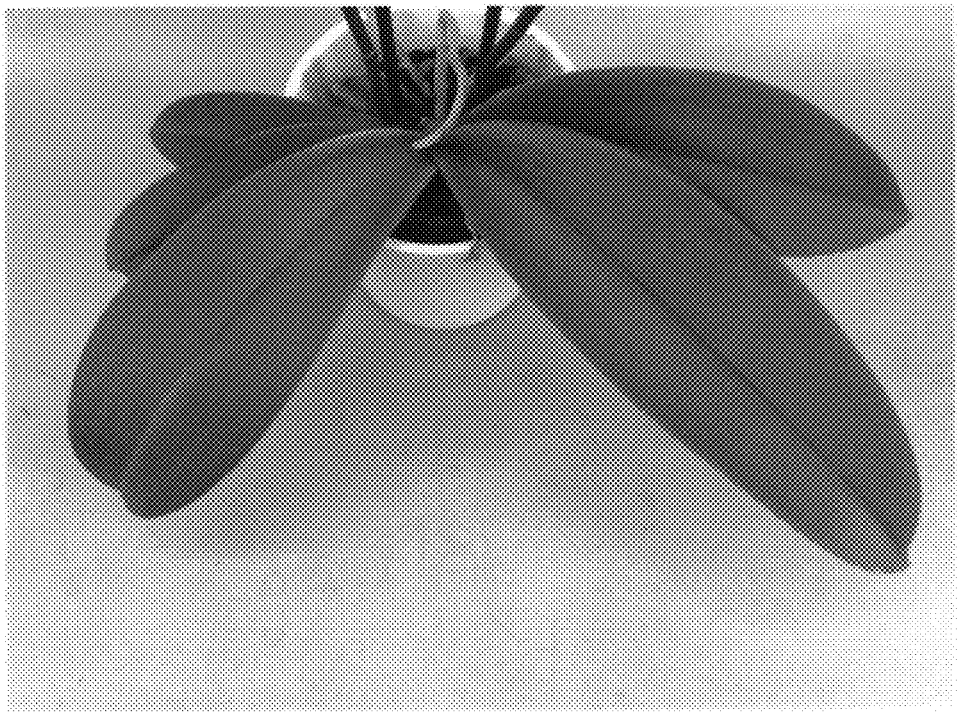
FIG. 3 shows an overhead view of the leaves of 'PHALGOSEP'.

The following detailed description sets forth the distinctive characteristics of 'PHALGOSEP'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in July 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29 ° C. for 30 weeks, continued by a cooling period of 8 weeks between 18° C. to 20° C. and 12 weeks in a greenhouse of 21° C. Flowering occurs after 50-weeks in a 12 centimeter pot.

DETAILED BOTANICAL DESCRIPTION

Classification:
- *Family.*—Orchidaceae.
- *Botanical.*—*Phalaenopsis* hybrid.
- *Common name.*—Moth orchid.
- *Variety name.*—'PHALGOSEP'.

Parentage:
- *Female parent.*—*Phalaenopsis* cultivar '01-1988' (unpatented).
- *Male parent.*—*Phalaenopsis* cultivar '01-3401' (unpatented).

Propagation:
- *Type.*—Meristem tissue culture.

Roots:
- *Root description.*—Greyed-green colored roots (RHS 190B/C) with branching lateral roots having light green (RHS 144C) colored root tips.

Plant:
- *Commercial crop time to flowering.*—Following asexual propagation (in-vitro), the rooted cuttings grow for 20-24 weeks. After transplantation into 12 cm pots, the plants are finished after 48 to 50 weeks.
- *Growth habit of peduncle.*—Upright to slightly pendant with raceme to panicle inflorescence.
- *Height* (*from soil level to top of inflorescence*).—Approximately 51.0 cm to 61.0 cm.
- *Width* (*measured from leaf tips*).—About 35.0 cm to 37.0 cm.
- *Vigor.*—Strong.

Leaves:
- *Mature leaves.*—Quantity per plant: 7 to 8 leaves are produced before flowering. Length (fully expanded): 24.0 cm to 27.0 cm. Width: 8.0 cm to 9.0 cm. Shape: Oblong. Base shape: Elongated. Apex: Obtuse unequal. Leaf blade angle with the petiole (measured from the horizontal position): Between 10 degrees and 20 degrees. Leaf margin: Entire. Color: Upper surface: RHS 146A. Lower surface: RHS 146B. Texture (upper surface): Rough. Thickness: 2.4 mm to 2.7 mm. Venation: Pattern: Parallel. Color of the midvein: Upper surface: RHS 146A. Lower surface: RHS 146B.

Peduncle:
- *Quantity per plant.*—1 to 2.
- *Number of flowers per peduncle.*—14 to 20.
- *Length.*—51.0 cm to 61.0 cm.
- *Diameter.*—5.7 mm to 6.3 mm.
- *Strength.*—Strong.
- *Aspect.*—Upright to slightly pendant.
- *Texture.*—Smooth.
- *Color.*—Green (RHS 146B) with a touch of brown (RHS N200A).
- *Internode length.*—4.0 cm to 7.0 cm.
- *Callosities.*—None.

Inflorescence description:
- *Appearance.*—Upright to slightly pendant, raceme to panicle inflorescence with bilaterally symmetrical flowers that open in succession beginning with the lowermost flower.
- *Inflorescence size.*—Height (from base to tip): 250.0 mm to 300.0 mm.
- *Flowering time.*—First flowers can be expected 10 to 11 months after planting in a 12 cm (diameter) pot.
- *Flower.*—Height: 82.0 mm to 87.0 mm. Diameter: 95.0 mm to 100.0 mm. Depth of lip: about 5.0 mm.
- *Flower longevity.*—On the plant: 13 to 17 weeks.
- *Fragrance.*—Absent.
- *Flower bud.*—Average size: Large. Length: 25.0 mm to 27.0 mm. Width: 19.0 mm to 21.0 mm. Shape: Egg shaped. Color: Light yellow-green (RHS 145C) with light reddish-purple shade (RHS N78D).
- *Petals.*—Arrangement: Open/free. Shape: Semi-circular. Apex: Rounded asymmetric. Margin: Slightly undulated. Length (from base to tip): 43.0 mm to 45.0 mm. Width: 56.0 mm to 58.0 mm. Color (when fully opened): Upper surface: Basic color: White (RHS NN155C). Over color: Absent. Lower surface: Basic color: White (RHS NN155C). Over color: Very light purple (RHS 76B).
- *Dorsal sepal.*—Shape: Elliptic. Apex: Obtuse symmetric. Margin: Entire. Length (from base to tip): 49.0 mm to 51.0 mm. Width: 31.0 mm to 33.0 mm. Color (when fully opened): Upper surface: Basic color: White (RHS NN155C). Over color: Absent. Lower surface: Basic color: White (RHS NN155C). Over color: Slightly light yellow-green (RHS 145D) and very light. purple (RHS 76B).
- *Lateral sepals.*—Shape: Ovate. Apex: Obtuse asymmetric. Margin: Entire. Length (from base to tip): 47.0 mm to 49.0 mm. Width: 27.0 mm to 29.0 mm. Color (when fully opened): Upper surface: Basic color: White (RHS NN155C). Over color: Few purplish-red stripes (RHS 185C) at the base. Lower surface: Basic color: White (RHS NN155C). Over color: Light yellow-green (RHS 145C) and purplish-pink middle vein (RHS 186C and 186D) toward the tip.
- *Labellum* (*lip*).—Overall shape: Three lobed with callus at central junction of the lateral lobes and base of the apical lobe. The apical lobe is terminated by 2 whiskers. Lateral lobes and apical lobes are connected.

*Lateral lobe.*—Margin: Undulated. Length: 24.0 mm to 26.0 mm. Width: 19.0 mm to 21.0 mm. Color: White (RHS NN155C) with red and purplish-red spots (RHS 182B and 186A) at the base.

*Apical lobe.*—Margin: Entire. Length: 24.0 mm to 26.0 mm. Width: 26.0 mm to 28.0 mm. Color: White (RHS NN155C) with purplish-pink shade (RHS N78C). Whiskers: Present. Length of whiskers: 4.0 mm to 6.0 mm. Color of whiskers: White (RHS NN155C).

*Callus.*—Average size: Medium to large. Height: 7.0 mm to 8.0 mm. Length: 6.0 mm to 7.0 mm. Width: 4.0 mm to 5.0 mm. Color: Light yellow-green (RHS 145C and 145D) dotted (RHS 177B).

Reproductive organs:

*Column.*—Length: 9.0 mm to 11.0 mm. Diameter: 5.5 mm to 5.7 mm. Color: White (RHS NN155C).

*Pollinia.*—Quantity: 2. Diameter: 1.2 mm to 1.4 mm. Color: Orange (RHS 24A).

*Ovary.*—Length: 10.0 mm to 12.0 mm. Diameter: 2.4 mm to 2.6 mm. Color: Very light purple (RHS 76C).

*Pedicel.*—Length: 34.0 mm to 36.0 mm. Diameter: 2.7 mm to 3.0 mm. Color: Green (RHS 146C) at the base; light yellow-green (RHS 145C) and very light purple (RHS 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGOSEP' differs from female parent plant '01-1988' (unpatented) in that 'PHALGOSEP' has an extra-large lip shape with the apical and lateral lobes connected, and white whiskers, whereas '01-1988' has a typical lip shape with the apical and lateral lobes separated, and yellow whiskers. Additionally, 'PHALGOSEP' has shorter whiskers than '01-1988'.

'PHALGOSEP' differs from male parent plant '01-3401' (unpatented) in that 'PHALGOSEP' has white flowers, white whiskers and obtuse dorsal sepal apices, whereas '01-3401' has reddish-purple flowers, reddish-purple whiskers and emarginated dorsal sepal apices.

'PHALGOSEP' is most similar to the commercial *Phalaenopsis* plants named 'PHALGAQCI' (unpatented) and 'PHALDANCIP' (unpatented). 'PHALGOSEP' differs from the commercial variety 'PHALGAQCI' in that 'PHALGOSEP' has white whiskers, white columns and an even flower pattern, whereas 'PHALGAQCI' has reddish-purple whiskers, reddish-purple columns and a striped and spotted flower pattern. Additionally, 'PHALGOSEP' has longer whiskers than 'PHALFGAQCI'.

'PHALGOSEP' differs from the commercial variety 'PHALDANCIP' in that 'PHALGOSEP' has white whiskers, white columns, an even flower pattern and an extra-large lip shape with the apical and lateral lobes connected, whereas 'PHALDANCIP' has light purple whiskers, white columns with a small light reddish-purple region toward the tip, a slightly striped flower pattern and a typical lip shape with the apical and lateral lobes separated. Additionally, 'PHALGOSEP' has shorter whiskers than 'PHALDANCIP'.

I claim:

1. A new and distinct variety of *Phalaenopsis* plant named 'PHALGOSEP', substantially as described and illustrated herein.

* * * * *